United States Patent [19]

Tsai et al.

[11] Patent Number: 5,756,610
[45] Date of Patent: May 26, 1998

[54] TITANIUM (III) BASES AND β-DIKETONATE COORDINATED CATALYST COMPOSITION FOR PREPARING HIGH-SYNDIOTACTICITY POLYSTYRENE AND PROCESSES USING THE SAME

[75] Inventors: Jing-Chemg Tsai; Kuang Kai Liu; Shu-Ling Peng; Shian-Jy Wang, all of Hsinchu, Taiwan

[73] Assignee: Industrail Technoloy Research Institute, Hsinchu

[21] Appl. No.: 781,705

[22] Filed: Jan. 10, 1997

[51] Int. Cl.$^6$ .................... C08F 4/16; C07F 7/28
[52] U.S. Cl. .................... 526/127; 526/126; 526/131; 526/132; 526/133; 526/134; 526/153; 526/159; 526/161; 526/346; 556/9; 556/12; 556/40; 556/41; 502/103; 502/104; 502/158; 502/171
[58] Field of Search ............ 556/9, 12, 40, 556/41; 526/126, 127, 132, 133, 134, 153, 159, 161; 502/103, 104, 158, 171

[56] References Cited

U.S. PATENT DOCUMENTS 3,505,369  4/1970  Deffiner .................. 556/41
3,946,057  3/1976  Reedy .................... 556/41 X
4,438,039  3/1984  Beers et al. .............. 556/40

*Primary Examiner*—Fred Teskin
*Attorney, Agent, or Firm*—W. Wayne Liauh

[57] ABSTRACT

A novel titanium (III)-based β-diketonate-coordinated compound is disclosed for catalyzing the polymerization reaction of syndiotactic polystyrenes. The titanium (III)-based compound is represented by the following formula 1:

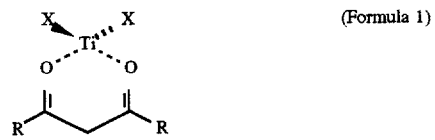

(Formula 1)

wherein X is a $C_1$-$C_{12}$ alkoxy or amine group, or a halogen atom; R is a $C_1$-$C_{12}$ alkyl, aryl, or alkylsilane group. Preferably, X is $N(SiMe_3)_2$— or OMe—, and R is phenyl, methyl, or t-butyl. The titanium (III)-based compounds are prepared by reacting titanium trichloride with diketone and tetrahydrofuran to form an intermediate product, then reacting the intermediate product $Ti(AcAc)Cl_2(THF)_2$ with either aminosilane or alcohol.

22 Claims, No Drawings

TITANIUM (III) BASES AND β-DIKETONATE COORDINATED CATALYST COMPOSITION FOR PREPARING HIGH-SYNDIOTACTICITY POLYSTYRENE AND PROCESSES USING THE SAME

FIELD OF THE INVENTION

The present invention relates to a novel catalyst composition for preparing high-syndiotacticity polystyrene polymers. More specifically, the present invention relates to a titatium (III)-based catalyst composition for preparing polystyrene polymers which does not contain cyclopentadiene as coordinating groups, while providing high activity and high syndiotacticity and at a lowered cost.

BACKGROUND OF THE INVENTION

Polystyrenes, or styrene-containing polymers in general, can be classified into three categories: atactic, isotactic, and syndiotactic. Syndiotactic polystyrenes exhibit the advantages of high melting point (270° C.), low density (1.04 kg/cm$^3$), low dielectric constant (2.6), high vicat softening temperature (254° C.), excellent chemical resistance and water (steam) resistance, and low moisture absorption. The above reported values are measured from a specific syndiotactic polystyrene under a specific set of conditions. These values, of course, are subject to change as a result of different polymer molecular weight and many other factors.

Typically, the polymerization of syndiotactic polystyrene requires a catalyst composition containing a transitional metal titanium complex and methyl aluminoxane (or "MAO"). The concerted actions of the titanium complex and the methyl aluminoxane allow syndiotactic polystyrene to be polymerized. The titanium complex used in polymerizing syndiotactic polystyrene is characterized in either being a titanium (IV), or containing cyclopentadiene as coordinating groups, or both. Examples of the titanium (IV) complexes include *CpTi(OMe)$_3$, CpTiCl$_3$, Ti(OEt)$_4$, TpTi(OiPr)$_3$, TiR'$_1$R'$_2$R'$_3$R'$_4$. The first three compounds were developed by Idemitsu, the fourth by Dow Chemicals, and the fifth by Union Chemical Laboratories (UCL), a division of Industrial Technology Research Institute of Taiwan (Cp=cyclopentadiene, and *Cp=pentamethyl cyclopentadiene). The compound of TiR'$_1$R'$_2$R'$_3$R'$_4$ is disclosed in a co-pending application Ser. No. 08/563,272; the content thereof is incorporated by reference. Examples of titanium (III) compounds are very rarely reported. One example is *CpTi(OMe)$_2$ developed by Dow Chemicals; it contains cyclopentadiene as a coordinating group.

Titanium (III) based catalysts for polymerizing syndiotactic polystyrene always require cyclopentadiene as a coordinating group. Because cyclopentadiene is a relatively expensive compound, it is desirable to develop other titanium (III) based catalysts for polymerizing syndiotactic polystyrene which do not require cyclopentadiene as coordinating group.

SUMMARY OF THE INVENTION

The primary object of the present invention is to develop a titanium (III) based catalyst for polymerizing syndiotactic polystyrene which does not require cyclopentadiene as coordinating group. More specifically, the primary object of the present invention is to develop a catalyst composition containing a titanium (III) based compound, which does contain cyclopentadiene as coordinating groups, for preparing polystyrene polymers, so as to substantially lower cost of the catalyst composition, while providing high catalytic activity and high syndiotacticity of the styrene-containing polymers.

The titanium (III) based compound disclosed in the present invention is represented by the following formula 1:

(Formula 1)

Where X is C$_1$–C$_{12}$ alkoxy group, amine group, or halogen atoms. The R In the β-diketonate can be a C$_1$–C$_{12}$ alkyl, aryl, or alkylsilane group. Preferably, X is amine (such as N(SiMe$_3$)$_2$—) or alkoxide (such as OMe—), and R is phenyl, methyl, or t-butyl group. In formula 1, the titanium is a three-valenced titanium (III).

Formula 1 can be abbreviated as Ti(AcAc)X$_2$, wherein AcAc is a β-diketonate represented by the following formula 2:

(Formula 2)

The novel titanium (III)-based and β-diketonate-coordinated compound disclosed in the present invention is prepared by first reacting Titanium trichloride with diketone in the presence of tetrahydrofuran (THF) to form a Ti(AcAc)Cl$_2$(THF)$_2$. The first reaction is summarized as follows:

In the preferred embodiments, the diketone, AcAc, can be one of the following:

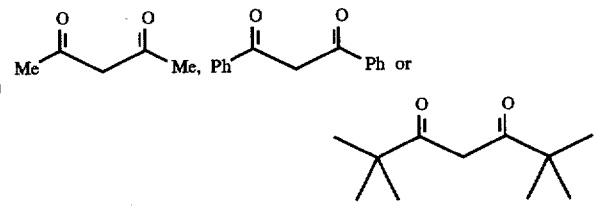

Where Me and Ph represent a methyl group and a phenyl group, respectively.

The Ti(AcAc)Cl$_2$(THF)$_2$ is then reacted with either silanoamine or alcohol to produce the titanium (III)-based and β-diketonate-coordinated compound of the present invention. The second reaction is summarized as follows:

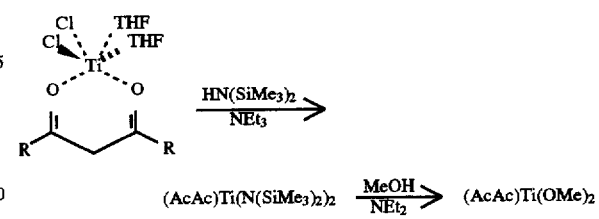

When the titanium (III)-based catalyst is used in the polymerization of syndiotactic polystyrenes, methyl aluminoxane (MAO) or borate can be used as a co-catalyst. At a reaction temperature of 70° C., the reactivity of the catalyst composition utilizing the titanium (III)-based catalyst can reach $1\times10^4$ (gSPS/gTih, grams of syndiotactic polystyrene per gram of Titanium per hour). The amount of MAO/Titanium required is at a favorably low value of about $5\times10^2$ (mole-Al/mole-Ti).

DETAILED DESCRIPTION OF THE PREFERRED EMBODIMENT

The present invention discloses a titanium (III)-based catalyst for polymerizing syndiotactic polystyrene which does not require cyclopentadiene as coordination group. The titanium (III) based compound disclosed in the present invention contains a β-diketonate coordination group, and is represented by the following formula 1:

(Formula 1)

In Formula 1, X can be $C_1$–$C_{12}$ alkoxy or aminosilane group, or a halogen atom. The radical R can be a $C_1$–$C_{12}$ alkyl, aryl, or alkylsilane group. Preferably, X is $N(SiMe_3)_2$— or OMe—, and R is phenyl, methyl, or t-butyl group. In Formula 1, the titanium is a three-valenced titanium (III). Formula 1 can be abbreviated as $Ti(AcAc)X_2$, wherein AcAc is a β-diketonate represented by the following formula 2:

(Formula 2)

The novel titanium (III)-based and β-diketonate-coordinated compound disclosed in the present invention can be prepared by first reacting titanium trichloride with diketone and tetrahydrofuran (THF) to form an intermediate product, $Ti(AcAc)Cl_2(THF)_2$. The first reaction is summarized as follows:

In the preferred embodiments, the diketone, AcAc, can be one of the following:

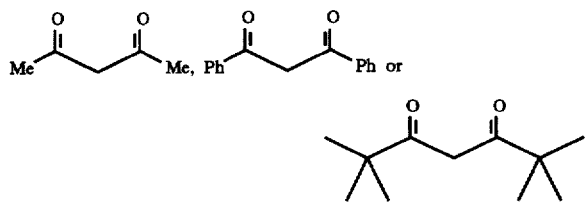

The $Ti(AcAc)Cl_2(THF)_2$ is then reacted with either aminosilane or alcohol to produce the titanium (III)-based and β-diketonate-coordinated compound of the present invention. The second reaction is summarized as follows:

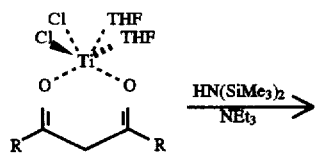

-continued

When the titanium (III)-based catalyst is typically used in conjunction with a co-catalyst, such as methyl aluminoxane (MAO) or borate, for the polymerization of syndiotactic polystyrenes. At a reaction temperature of 70° C., the reactivity of the catalyst composition utilizing the titanium (III)-based catalyst can reach $1\times10^4$ gSPS/gTih. The amount of MAO/Titanium required is at a favorably low value of about $5\times10^2$ (mole-Al/mole-Ti). The cocatalyst borate belongs to a group of non-coordinated Lewis acids. This type of cocatalyst can be a mixture containing 0.1 to 20 parts by mole of a non-coordinated Lewis acid (preferably a borate, such as N,N-dimethyl anilinium tetrakis (pentafluorophenyl) borate, triphenyl carbenium tetrakis (pentafluorophenyl)borate, and ferrocerium tetrakis (pentafluorophenyl)borate) and 100 to 10,000 parts by mole of a trialkyl aluminum such as triethyl aluminum or triisobutyl aluminum.

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1a

Synthesis of $Ti(AcAc)Cl_2(THF)_2$, AcAc=2,4-pentanedione 1.48 g (4 mmole) of $TiCl_3(THF)_3$ was added into a 100 ml round-bottomed flask, then 40 ml of THF was added and stirred. Thereafter, 0.45 g of 2,4-pentanedione was added and the reaction mixture was stirred at room temperature for two hours. After the reaction, the THF was removed at reduced pressure, and the dark blue reaction product was washed with pentane twice then dried in a vacuum chamber to obtain 1.33 g of dark blue reaction product. This represented a reaction yield of 92%.

EXAMPLE 1b

Synthesis of $Ti(AcAc)Cl_2(THF)_2$, AcAc=1,3-diphenyl-1,3-propanedione 1.48 g (4 mmole) of $TiCl_3(THF)_3$ was added into a 100 ml round-bottomed flask, then 40 ml of THF was added and stirred. Thereafter, 0.90 g of 1,3-diphenyl-1,3-propanedione was added and the reaction mixture was stirred at room temperature for six hours. After the reaction, the THF was removed at reduced pressure, and the dark green reaction product was washed with pentane twice then dried in a vacuum chamber to obtain 1.90 g of reaction product. This represented a reaction yield of 98%.

EXAMPLE 1c

Synthesis of $Ti(AcAc)Cl_2(THF)_2$, AcAc=2,2,6,6-tetramethyl-3,5-heptanedione 1.48 g (4 mmole) of $TiCl_3(THF)_3$ was added into a 100 ml round-bottomed flask, then 40 ml of THF was added and stirred. Thereafter, 0.74 g of 2,2,6,6-tetramethyl-3,5-heptanedione was added and the reaction mixture was stirred at room temperature for six hours. After the reaction, the THF was removed at reduced pressure, and the dark red reaction product was washed with pentane twice then dried in a vacuum chamber to obtain 1.71 g of reaction product. This represented a reaction yield of 96%.

EXAMPLE 2a

Synthesis of $(AcAc)Ti[N(SiMe_3)_2]_2$, $AcAc=2,4$-pentanedione 1.09 g (3.0 mmole) of $Ti(AcAc)Cl_2(THF)_2$, $AcAc=2,4$-pentanedione, prepared in Example 1a, was immersed into 40 ml of toluene. Then, 0.50 g of $Li[N(SiMe_3)_2]$ was added and the reaction mixture was stirred at room temperature for six hours. After the reaction, the white precipitate LiCl was removed by filtration. The white precipitate was extracted with toluene twice. The extractant and the filtrate were mixed and dried under vacuum to obtain 1.01 g of deep blue reaction product. This represented a reaction yield of 72% (EPR:singlet 1.96 G).

EXAMPLE 2b

Synthesis of $(AcAc)Ti(OMe)_2$, $AcAc=2,4$-pentanedione 1.09 g (3.0 mmole) of $Ti(AcAc)Cl_2(THF)_2$, $AcAc=2,4$-pentanedione, prepared in Example 1a, was immersed into 40 ml of toluene. Then, 0.24 ml of methanol and 0.84 ml of ethylamine were added and the reaction mixture was stirred at room temperature for twelve hours. After the reaction, the precipitate of triethylamine acid salt was removed by filtration. The precipitate was extracted with toluene twice. The extractant and the filtrate were mixed and dried under vacuum to obtain 0.41 g of deep blue reaction product. This represented a reaction yield of 65% (EPR:singlet 1.92 G).

EXAMPLE 2c

Synthesis of $(AcAc)Ti(OMe)_2$, $AcAc=1,3$-diphenyl-1,3-propanedione 1.49 g (3.0 mmole) of $Ti(AcAc)Cl_2(THF_2$, $AcAc=1,3$-diphenyl-1,3-propanedione, prepared in Example 1b, was immersed into 40 ml of toluene. Then, 0.24 ml (6 mmole) of methanol and 0.84 ml (6 mmole) of ethylamine were added and the reaction mixture was stirred at room temperature for twelve hours. After the reaction, triethylamine acid salt precipitate was removed by filtration. The precipitate was extracted with toluene twice. The extractant and the filtrate were mixed and dried under vacuum to obtain 0.82 g of dark green reaction product. This represented a reaction yield of 82% (EPR:singlet 1.80 G).

EXAMPLE 2d

Synthesis of $(AcAc)Ti(OMe)_2$, $AcAc=2,2,6,6$-tetramethyl-3,5-heptanedione 1.34 g (3.0 mmole) of $Ti(AcAc)Cl_2(THF)_2$, $AcAc=2,2,6,6$-tetramethyl-3,5-heptanedione, prepared in Example 1c, was immersed into 40 ml of toluene. Then, 0.24 ml (6 mmole) of methanol and 0.84 ml (6 mmole) of ethylamine were added and the reaction mixture was stirred at room temperature for twelve hours. After the reaction, triethylamine acid salt precipitate was removed by filtration. The precipitate was extracted with toluene twice. The extractant and the filtrate were mixed and dried under vacuum to obtain 0.49 g of deep blue reaction product. This represented a reaction yield of 56% (EPR:singlet 1.97 G).

EXAMPLE 3a

Polymerization of Syndiotactic Polystyrene Polymers Using $(AcAc)Ti[N(SiMe_3)_2]_2$, $AcAc=2,4$-pentanedione As Catalyst A 1-liter glass polymerization vessel was evacuated under elevated temperature, then filled with nitrogen. 400 ml of styrene and 8 ml methyl aluminoxane (1.5M in toluene) were added into the polymerization vessel. The temperature of the reaction mixture was raised to 70 °C., then 2.5 ml of the titanium (III) based catalyst prepared in Example 2a, $(AcAc)Ti[N(SiMe_3)_2]_2$, $AcAc=2,4$-pentanedione, (0.016M in toluene) was added to begin the polymerization reaction, which lasted two hours at 70° C. The feeding steps and polymerization reaction all took places under nitrogen. At the end of the two hour period, 150 ml of methanol was added to stop the polymerization reaction. The white reaction product was filtered and dried to obtain 2.30 g of syndiotactic polystyrene resin. The catalyst activity was calculated to be $6.0 \times 10^2$ gSPS/gTih. The syndiotactic polystyrene resin so produced had a melting point of 266° C., and an MIP (MEK-insoluble portion) of 76%.

EXAMPLE 3b

Polymerization of Syndiotacticity Polystyrene Polymers Using $(AcAc)Ti[N(SiMe_3)_2]_2$, $AcAc=2,4$-pentanedione as a Catalyst A 1-liter glass polymerization vessel was evacuated under elevated temperature, then filled with nitrogen. 400 ml of styrene and 8 ml methyl aluminoxane (1.5M in toluene) were added into the polymerization vessel. The temperature of the reaction mixture was raised to 70° C., then 2.5 ml of the titanium (III) based catalyst prepared in Example 2b, $(AcAc)Ti[N(SiMe_3)_2]_2$, $AcAc=2,4$-pentanedione, (0.016M in toluene) was added to begin the polymerization reaction, which lasted two hours at 70° C. The feeding steps and polymerization reaction all took places under nitrogen. At the end of the polymerization reaction, 150 ml of methanol was added to stop the polymerization reaction. The white reaction product was filtered and dried to obtain 5.9 g of syndiotactic polystyrene resin. The catalyst activity was calculated to be $3.1 \times 10^3$ gSPS/gTih. The syndiotactic polystyrene resin so produced had a melting point of 266° C., and an MIP (MEK-insoluble portion) of 78%.

EXAMPLE 3c

Polymerization of Syndiotacticity Polystyrene Polymers Using $(AcAc)Ti(OMe)_2$, $AcAc=1,3$-diphenyl-1,3-propanedione as a Catalyst The procedure in Example 3c was identical to those in Examples 3a and 3b, except $(AcAc)Ti(OMe)_2$, $AcAc=1,3$-diphenyl-1,3-propanedione was used as the primary catalyst. After reacting at 60° C. for two hours, 13.8 g of syndiotactic polystyrene resin was obtained. The catalyst activity was calculated to be $7.2 \times 10^3$ gSPS/gTih. The syndiotactic polystyrene resin so produced had a melting point of 269° C., and an MIP (MEK-insoluble portion) of 89%.

EXAMPLE 3d

Polymerization of Syndiotacticity Polystyrene Polymers Using $(AcAc)Ti(OMe)_2$, $AcAc=1,3$-diphenyl-1,3-propanedione as a Catalyst The procedure in Example 3d was identical to those in Examples 3a and 3b, except $(AcAc)Ti(OMe)_2$, $AcAc=1,3$- diphenyl-1,3-propanedione was used as the primary catalyst and the reaction temperature was at 80° C. 24.9 g of syndiotactic polystyrene resin was obtained. The catalyst activity was calculated to be $1.3 \times 10^4$ gSPS/gTih. The syndiotactic polystyrene resin so produced had a melting point of 269° C., and an MIP (MEK-insoluble portion) of 86%.

EXAMPLE 3e

Polymerization of Syndiotacticity Polystyrene Polymers Using $(AcAc)Ti(OMe)_2$, AcAc=2,2,6,6-tetramethyl-3,5-heptanedione as a Catalyst The procedure in Example 3d was identical to those in Examples 3a and 3b, except $(AcAc)Ti(OMe)_2$, AcAc=2,2,6,6-tetramethyl-3,5-heptanedione was used as the primary catalyst and the reaction temperature was at 70° C. 10.0 g of syndiotactic polystyrene resin was obtained. The catalyst activity was calculated to be $5.2 \times 10^3$ gSPS/gTih. The syndiotactic polystyrene resin so produced had a melting point of 270° C., and an MIP (MEK-insoluble portion) of 82%.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A titanium (III)-based β-diketonate-coordinated compound represented by the following formula 1:

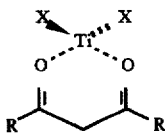
(Formula 1)

wherein

X is a $C_1$–$C_{12}$ alkoxy or aminosilane group;

R is a $C_1$–$C_{12}$ alkyl, aryl, or alkylsilane group.

2. The titanium (III)-based β-diketonate-coordinated compound according to claim 1 wherein X is $N(SiMe_3)_2$— or OMe—.

3. The titanium (III)-based β-diketonate-coordinated compound according to claim 1 wherein X is $N(SiMe_3)_2$—.

4. The titanium (III)-based β-diketonate-coordinated compound according to claim 1 wherein X is OMe—.

5. The titanium (III)-based β-diketonate-coordinated compound according to claim 1 wherein R is phenyl, methyl, or t-butyl group.

6. A catalyst composition for preparing syndiotactic polystyrene which does not require a cyclopentadiene coordination group, said catalyst composition comprising:

(a) 0.1 to 10 parts by mole of a titanium (III)-based β-diketonate-coordinated compound represented by the following formula 1;

(Formula 1)

wherein

X is a $C_1$–$C_{12}$ alkoxy or aminosilane group;

R is a $C_1$–$C_{12}$ alkyl, aryl, or alkylsilane group;

(b) a cocatalyst comprising methyl aluminoxane, at 20 to 20,000 parts by mole, or borate, at 0.1 to 20 parts also by mole.

7. The catalyst composition for preparing syndiotactic polystyrene according to claim 6 wherein X is $N(SiMe_3)_2$— or OMe—.

8. The catalyst composition for preparing syndiotactic polystyrene according to claim 6 wherein X is $N(SiMe_3)_2$—.

9. The catalyst composition for preparing syndiotactic polystyrene according to claim 6 wherein X is OMe—.

10. The catalyst composition for polymerizing syndiotactic polystyrene according to claim 6 wherein R is phenyl, methyl, or t-butyl group.

11. A process for preparing syndiotactic polystyrene comprising the step of mixing styrene monomers with a catalyst composition, said catalyst composition comprising;

(a) 0.1 to 10 parts by mole of a titanium (III)-based β-diketonate-coordinated compound represented by the following formula 1:

(Formula 1)

wherein

X is a $C_1$–$C_{12}$ alkoxy or aminosilane group;

R is a $C_1$–$C_{12}$ alkyl, aryl, or alkylsilane group;

(b) a cocatalyst comprising methyl aluminoxane, at 20 to 20,000 parts by mole, or borate, at 0.1 to 20 parts by mole.

12. The process for preparing syndiotactic polystyrene according to claim 11 wherein X is $N(SiMe_3)_2$— or OMe—.

13. The process for preparing syndiotactic polystyrene according to claim 11 wherein X is $N(SiMe_3)_2$—.

14. The process for preparing syndiotactic polystyrene according to claim 11 wherein X is OMe—.

15. The process for preparing syndiotactic polystyrene according to claim 11 wherein R is phenyl, methyl, or t-butyl group.

16. The process for polymerizing syndiotactic polystyrene according to claim 11 wherein said cocatalyst is a mixture containing:

(a) 0.1 to 20 parts by mole of a borate, which is selected from the group consisting of N,N-dimethyl anilinium tetrakis (pentafluorophenyl) borate, triphenyl carbenium tetrakis(pentafluorophenyl) borate, and ferrocerium tetrakis(pentafluorophenyl) borate; and (b) 100 to 10,000 parts by mole of a trialkyl aluminum.

17. A method for making titanium (III)-based β-diketonate-coordinated compounds comprising the following step of reacting $Ti(AcAc)Cl_2(THF)_2$, wherein AcAc represents a diketonate, with either amine or alcohol to produce said titanium (III)-based and β-diketonate-coordinated compound, which is represented by the following formula 1:

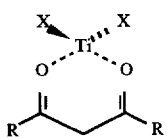
(Formula 1)

wherein

X is a $C_1$~$C_{12}$ alkoxy or aminosilane group;

R is a $C_1$~$C_{12}$ alkyl aryl, or alkylsilane group.

18. The process for making titanium (III)-based β-diketonate-coordinated compound according to claim 17 wherein X is N(SiMe$_3$)$_2$— or OMe—.

19. The process for making titanium (III)-based β-diketonate-coordinated compound according to claim 17 wherein X is N(SiMe$_3$)$_2$—.

20. The process for making titanium (III)-based β-diketonate-coordinated compound according to claim 17 wherein X is OMe—.

21. The process for making titanium (III)-based β-diketonate-coordinated compound according to claim 17 wherein R is phenyl, methyl, or t-butyl group.

22. The process for making titanium (III)-based β-diketonate-coordinated compound according to claim 17 wherein said Ti(AcAc)Cl$_2$(THF)$_2$ is obtained by reacting titanium trichloride with diketone and tetrahydrofuran (THF).

* * * * *